(12) United States Patent
Kim et al.

(10) Patent No.: US 8,318,199 B2
(45) Date of Patent: Nov. 27, 2012

(54) LIPOSOME FOR LIVER-SPECIFIC DELIVERY AND RELEASE OF THERAPEUTIC NUCLEIC ACIDS OR DRUGS

(75) Inventors: Meehyein Kim, Yongin-si (KR); Soo In Kim, Yongin-si (KR); Duckhyang Shin, Yongin-si (KR); Mahnhoon Park, Yongin-si (KR)

(73) Assignee: Mogam Biotechnology Research Institute, Yongin-si (KR)

( * ) Notice: Subject to any disclaimer, the term of this patent is extended or adjusted under 35 U.S.C. 154(b) by 0 days.

(21) Appl. No.: 12/791,600

(22) Filed: Jun. 1, 2010

(65) Prior Publication Data

US 2010/0239657 A1    Sep. 23, 2010

Related U.S. Application Data

(62) Division of application No. 11/741,287, filed on Apr. 27, 2007, now abandoned.

(30) Foreign Application Priority Data

Nov. 9, 2006    (KR) .................. 10-2006-0110402

(51) Int. Cl.
*A61K 9/127*    (2006.01)
*C12N 15/88*    (2006.01)
*A61K 48/00*    (2006.01)

(52) U.S. Cl. ........ 424/450; 435/458; 977/907; 514/44 R

(58) Field of Classification Search .................. None
See application file for complete search history.

(56) References Cited

U.S. PATENT DOCUMENTS

| | | | |
|---|---|---|---|
| 7,402,404 B2 | 7/2008 | Rothblat et al. | |
| 2005/0008617 A1 | 1/2005 | Chen et al. | |
| 2005/0042632 A1 | 2/2005 | Radka | |
| 2005/0222064 A1 | 10/2005 | Vargeese et al. | |
| 2006/0008910 A1 | 1/2006 | MacLachlan et al. | |
| 2006/0019912 A1 | 1/2006 | Burkoth et al. | |

FOREIGN PATENT DOCUMENTS

WO    99/17740 A1    4/1999

OTHER PUBLICATIONS

Kim, et al. (Jun. 2007) "Systemic and Specific Delivery of Small Interfereing RNAs to the Liver Mediated by Apolipoprotein A-I", Molecular Therapy, 15(6): 1145-52. (First available online Apr. 18, 2007.).*
Kim, et al. (2009) "Targeted delivery of siRNA against hepatitis C virus by apolipoprotein A-I-bound cationic liposomes", Journal of Hepatology, 50: 479-488. (First available online Dec. 27, 2008.).*
Lee (2004) "How lipids affect the activities of integral membrane proteins", Biochimica et Biophysica Acta, 1666: 62-87.*
Morrissey, D.V., et al., "Potent and persistent in vivo anti-HBV activity of chemically modified siRNAs," Nature Biotechnology, Aug. 2005, vol. 23, No. 8, pp. 1002-1007.
Zimmermann, T.S. et al., "RNAi-mediated gene silencing in non-human primates," Nature, May 4, 2006, vol. 44, pp. 1111-1114.
Kim et al., "Molecular Therapy," 2007, vol. 15(6), pp. 1145-1152.
Lou et al., "World Journal of Gastroenterology," 2005, vol. 11(7), pp. 954-959.
Liu et al., "Biochemistry," 1990, vol. 29(15), pp. 3637-3643.

\* cited by examiner

*Primary Examiner* — Robert M Kelly
(74) *Attorney, Agent, or Firm* — Sughrue Mion, PLLC

(57) ABSTRACT

Disclosed herein is a composite of a nanoscale particle size. The composite is able to specifically deliver therapeutic agents such as therapeutic nucleic acids or drugs to the liver and selectively release them into hepatic cells to manifest potent therapeutic effects of the therapeutic agents. The composite may be comprised of an apolipoprotein A-1 and a liposome-forming material. A composition containing the composite and a pharmaceutically acceptable carrier is disclosed.

8 Claims, 6 Drawing Sheets
(6 of 6 Drawing Sheet(s) Filed in Color)

LIPOSOME FOR LIVER-SPECIFIC DELIVERY AND RELEASE OF THERAPEUTIC NUCLEIC ACIDS OR DRUGS

The present application is a Divisional of U.S. application Ser. No. 11/741,287, filed Apr. 27, 2007, which claims priority to Korean Patent Application No. 10-2006-0110402 filed on Nov. 9, 2006. The entire disclosures of the prior applications are hereby incorporated by reference.

FIELD OF THE INVENTION

The present invention relates to a composite for liver-specific delivery of a therapeutic nucleic acid or a drug, a process for preparing the same and a composition comprising the same with a pharmaceutically acceptable carrier.

BACKGROUND OF THE INVENTION

A tissue-specific gene and drug delivery system has long been considered important for drug discovery and pharmaceutical advancement because most drugs are systemically delivered and circulated in the body when administered to a patient, which might adversely affect healthy organs or cells. The tissue-specific delivery system allows the accumulation of a high drug concentration at the target tissue which eliminating adverse side effects, leading to efficient treatment of tissue-specific diseases.

Some liver diseases arise from infection by pathogenic viruses, e.g., HBV (hepatitis B virus) and HCV (hepatitis C virus), while non-infectious liver diseases result from exposure to liver-toxic materials, or genetic or environmental disorders. The progression of early-stage liver diseases caused by biological stimuli ultimately leads to chronic hepatitis, liver cirrhosis or hepatocellular carcinoma (HCC). Among several drug or gene delivery systems currently studied in the treatment of such liver diseases, a lipoprotein system, mainly that of HDL. (high density lipoprotein), has advantages over other delivery systems which use viral vectors (Wang X., et al., *Gene Ther* (2006), 13: 1097-1103), non-viral complexes (Landen C. N., et al., *Cancer Res.* (2005), 65: 6910-6918; Morrissey D. V., et al., *Nat. Biotechnol.* (2005), 23: 1002-1007; Sorensen D. R., et al., *J. Mol. Biol.* (2003), 327: 761-766; and Urban-Klein B., et al., *Gene Ther* (2005), 12: 461-466) and antibodies (Song E., et al., *Nat. Biotechnol.* (2005), 23: 709-717). For example, the lipoprotein can be preferably recognized and taken up via cell surface receptors specific for liver cells (Firestone R. A., *Bioconjug. Chem.* (1994), 5: 105-113; de Smidt P. C., et al., *Crit. Rev. Ther. Drug Carrier Syst.* (1990), 7: 99-120; and Filipowska D., et al., *Cancer Chemother Pharmacol.* (1992), 29: 396-400), and it is an endogenous product which is not detrimental to human and does not trigger immunological responses in clinical applications (Pussinen P. J., et al., *Biochem. Biophys. Acta.* (2000), 1485: 129-144).

Recently, there has been a report that a recombinant high density lipoprotein (HDL) can be used as a carrier for delivering a lipophilic antitumor drug into human hepatocellular carcinoma cells by taking advantage of the hydrophobic cholesterol ester-loading properties of HDL (Lou B., et al., World J. Gastroenterol. (2005), 11: 954-959). However, it has merely been demonstrated in vitro, but not in vivo, that the cellular uptake of the HDL carrier by a hepatoma cell line, SMMC-7721, is higher in compared with a normal liver cell line, L02, and the limitation in tissue-specific targeting remains to be solved.

The present inventors have therefore endeavored to develop an effective system for liver-specific delivery of a therapeutic drug, and have found that a composite comprising an apolipoprotein A-I and a liposome-forming material can specifically deliver and release therapeutic drugs to the liver.

SUMMARY OF THE INVENTION

Accordingly, it is an object of the present invention to provide a composite capable of specifically delivering and releasing a therapeutic nucleic acid or a drug to the liver when administered via a systemic route.

It is another object of the present invention to provide a process for the preparation of said system.

It is further object of the present invention to provide a composition for liver-specific delivery of a therapeutic nucleic acid or drug, comprising said composite.

In accordance with one aspect of the present invention, there is provided a composite comprising an apolipoprotein A-I (Apo A-I) and a liposome-forming material.

In accordance with another aspect of the present invention, there is provided a process for the preparation of the composite.

In accordance with further another aspect of the present invention, there is provided a composition comprising the composite and a pharmaceutically acceptable carrier.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above and other objects and features of the present invention will become apparent from the following description of the invention, when taken in conjunction with the accompanying drawings, which respectively show.

DETAILED DESCRIPTION OF THE INVENTION

Figure 1A:
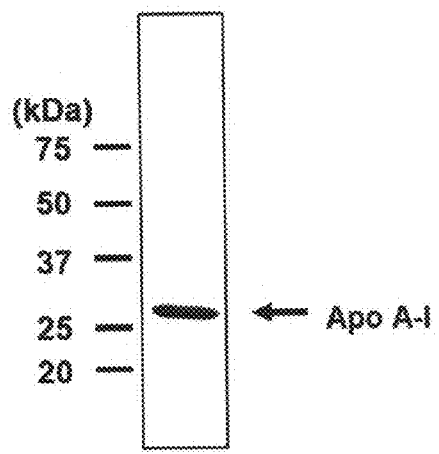
FIG. 1A: Purified human Apo A-I from adult blood separated by 4-20% sodium dodecyl sulfate-polyacrylamide gel electrophoresis.

The composite of the present invention may be in the form of nanoparticles having an average particle size ranging from 50 to 400 nm, preferably 100 to 250 nm, and the apolipoprotein A-I (Apo A-I) used in the present invention may be obtained from human blood by cold ethanol precipitation in accordance with a conventional method (e.g., Lerch, P. G., et al., *Vox. Sang.* (1996), 71: 155-164).

The liposome-forming material employed in the inventive composite may be a cationic or neutral liposome-forming material, or a mixture thereof, which play a role of avoiding undesirable interactions between the inventive composite and unknown serum components. Representative examples of the cationic liposome-forming material include DOTAP (1,2-dioleoyl-3-trimethylammonium-propane), DC-cholesterol (3β-[N—(N',N'-dimethylaminoethane)-carbamyl]cholesterol), DDAB (dimethyldioctadecylammonium bromide), and a mixture thereof, and the neutral liposome-forming material may be DOPE (L-alpha-dioleoyl phosphatidylethanolamine), cholesterol, or a mixture thereof.

The inventive composite may comprise Apo A-I and the liposome-forming material at a weight ratio ranging from 1:0.1 to 1:1000, preferably 1:1 to 1:100.

The composite of the present invention may further comprise a therapeutic nucleic acid and/or drug.

The therapeutic nucleic acid may be a DNA such as plasmid and PCR product, an RNA such as siRNA and ribozyme, or a derivative thereof obtained by chemical modification, preferably siRNA specific for HBV or HCV genome.

The therapeutic drug may be an active polypeptide, anticancer agent, or antivirus agent, which does not limit the scope of the present invention.

The active polypeptide used in the inventive composition may be selected from the group consisting of epidermal growth factor (EGF), erythropoietin (EPO), coagulation factors VIII, IX and VIIa, follicle stimulating hormone (FSH), granulocyte colony-stimulating factor (GCSF), granulocyte-macrophage colony stimulating factor (GM-CSF), insulin, insulin-like growth factor (IGF), interferon-α, -β and -γ (IFN-α, -β and -γ), interleukin-1, -2, -11, -12 and -15 (IL-1, -2, -11, -12 and -15), parathyroid hormone (PTH), platelet-derived growth factor (PDGF), human growth hormone (hGH), tissue plasminogen activator (tPA), vascular endothelial growth factor (VEGF), and a mixture thereof, which does not limit the scope of the present invention.

Further, the anticancer agent may be selected from the group consisting of carboplatin, cisplatin, oxaliplatin, heptaplatin, etoposide, semustine, hydroxycarbamide, citarabine, fludarabine, doxorubicin, epirubicin, idarubicin, pirarubicin, fluorouracil (5-FU), fluoxuridine, mitomycin, bleomycin, clofazimine, interferon, streptozocin, gemcitabine, enocitabine, capecitabine, ursodeoxycholic acid, sorafenib, tegafur, holmium and a holmium-chitosan complex, and the antivirus agent may be selected from the group consisting of atazanavir, ribavirin, zanamivir, acyclovir, entecavir, didanosin, nevirapine, valaciclovir, nelfinavir, efavirenz, ganciclovir, lamivudine, famciclovir, stavudine, abacavir, indinavir, oseltamivir, inosiplex, and adefovir, which does not limit the scope of the present invention.

The composite of the present invention may be prepared by a method comprising (i) dispersing liposome-forming materials in an organic solvent to form a liposome, (ii) dispersing the liposome in a dextrose solution, and sonicating the mixture to obtain a liposome suspension, and (iii) adding a solution containing Apo A-I thereto to allow forming the inventive composite. The method of the present invention may further comprise (iv) adding a therapeutic nucleic acid or a drug to the suspension of the inventive composite obtained in step (iii).

In accordance with further aspect of the present invention, there is provided a composition for liver-specific delivery of a therapeutic nucleic acid or drug, comprising the inventive composite and a pharmaceutically acceptable carrier. The inventive composition may further comprise the therapeutic nucleic acid or drug as described above.

The composition of the present invention may be formulated for oral or parenteral administration according to any one of the procedures well known in the art, so as to take the form of sterilized aqueous solution, hydrophobic solvent, suspension, emulsion, lyophilized formulation or suppository. In the formulation of the inventive composition, the hydrophobic solvent or suspension may further comprise a vegetable oil such as propylene glycol, polyethylene glycol and olive oil; an ester such as ethyloleate; or a mixture thereof, and the suppository may further comprise witepsol, macrogol, Tween 61, cacao butter, laurel oil, glycerol, gelatine, or a mixture thereof.

Further, a proposed daily dose of the composition of the present invention for administration to a human (of approximately 70 kg body weight) is about from 0.1 mg to 1000 mg, more preferably about from 1 mg to 500 mg. It should be understood that the daily dose should be determined in light of various relevant factors including the condition to be treated, the severity of the patient's symptoms, the route of administration, or the physiological form of the anticancer agent; and, therefore, the dosage suggested above does not limit the scope of the invention in anyway.

The following Examples are intended to further illustrate the present invention without limiting its scope.

TEST EXAMPLE 1

Liver-Specificity of Purified Apo A-I

High purity human apolipoprotein A-I (Apo A-I, 28 kDa) was obtained from serum fractions of normal healthy adults not infected with viral pathogens such as HBV, HCV or HIV by cold ethanol precipitation according to the established protocol (Lerch, P. G., et al., *Vox. Sang.* (1996), 71: 155-164).

After sodium dodecyl sulfate-polycrylamide gel electrophoresis (SDS-PAGE), and the purified Apo A-I was characterized by Coomassie blue staining. The result is shown in FIG. 1A. The identity of the purified Apo A-I was confirmed by western blot analysis using a goat anti-human Apo A-I antibody (Academy Biomedical Company, USA) which has cross-reactivity to mouse Apo A-I, and a secondary antibody, rabbit anti-goat IgG-HRP (KPL, USA).

For in vivo imaging, the purified protein (0.6 mg) was labeled with an infrared dye using IRDye 800 CW in vivo imaging agent (LI-COR Biosciences, USA), and purified using a dextran desalting column (Pierce Biotechnology, Inc., USA) to remove unincorporated dye. The labeled Apo A-I (200 µg) was administered to 6- to 8-week-old female nude mice (Charles River Laboratories, Inc., USA) via tail vein injection. After 7, 40, 90, 150, 240 or 360 min, the test mice anesthetized with 2% isoflurane were placed in a supine position in a light tight chamber, and their whole body images were obtained using IVIS 200 imaging system (Xenogen, USA) and Living Image Software (Xenogen, USA). The resulting images are shown in FIG. 1B.

Figure 1B:
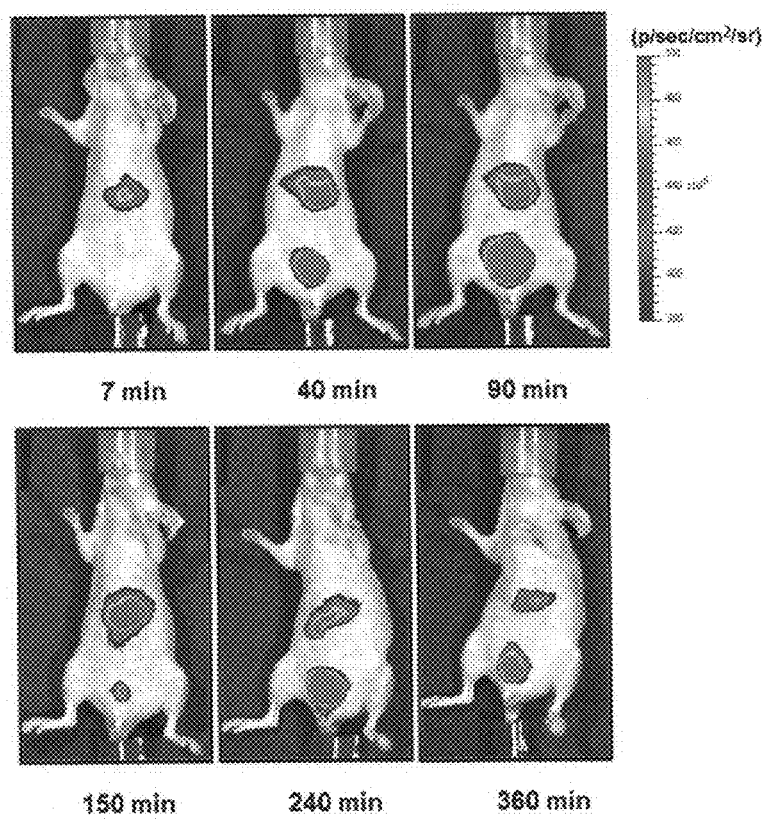
FIG. 1B: In vivo images of a mouse intravenously injected with Apo A-I labeled with an infrared fluorescent dye at several times after the injection.

As shown in FIG. 1B, Apo A-I can be specifically delivered to and stably maintained in the liver for at least 6 hours when systemically administered.

Figure 1C:
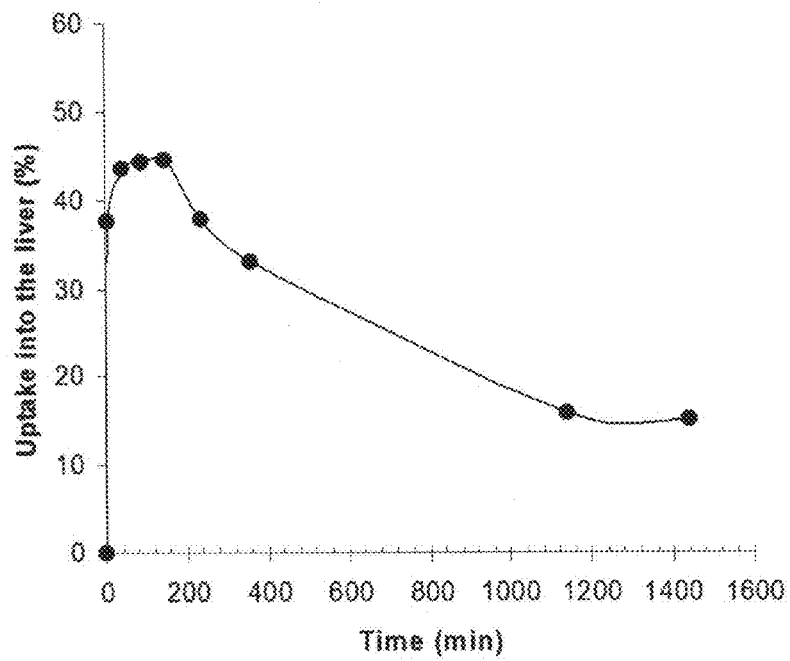
FIG. 1C: Percent uptake rate of Apo A-I in the livers of mice injected with Apo A-I at different time points (n=4) after the injection.

Further, the photon intensities in the liver of the test mice were measured using Living Image Software (Xenogen, USA) at each time point after the administration, and the result is shown in FIG. 1C.

FIG. 1C reveals that the uptake yield of the administered Apo A-I by liver are maximal at approximately 45% within 150 min after administration.

Taken together, these data demonstrate that the purified Apo A-I maintains its native conformation required for cell-surface receptor recognition and catabolic circulation in vivo, suggesting that it might be applicable as a potent candidate carrier for targeting the liver in feasibility studies for therapeutic drug delivery.

EXAMPLE 1

Preparation of the Inventive Composite

An equimolar mixture of 1,2-dioleoyl-3-trimethylammonium-propane (DOTAP; Avanti Polar Lipids, USA) and cholesterol (Sigma, USA) was dispersed in chloroform and mixed to form a cationic liposome of DOTAP/cholesterol (DTC). After the liposome assembly was formed, the organic solvent was removed by evaporation under a stream of $N_2$ gas and the residue was kept in a vacuum desiccator for 2 hours to ensure the removal of the residual organic solvent. The resulting dried film was hydrated in a 5% dextrose solution and the suspension thus obtained was sonicated using a bath sonicator. A solution containing 10% the Apo A-I purified in Test Example 1 was added thereto at a DTC:Apo A-I mix ratio of 10:1 (w/w), and the mixture was kept overnight at 4° C. to obtain the inventive composite (DTC-Apo).

EXAMPLE 2

Preparation of the Inventive Composite Containing Nucleic Acid

40 µg of HBV X gene-specific siRNA (SEQ ID NOs: 1 (sense) and 2 (antisense); Shin, D., Virus Res. (2006), 119: 146-153) was mixed with 400 µg of the inventive composite, DTC-Apo, in 200 µl of 5% dextrose solution and the mixture was incubated at room temperature for 30 min, to obtain the inventive composite containing HBV X gene-specific siRNA, named DTC-Apo/siHBV.

EXAMPLE 3

Preparation of the Inventive Composite Containing Nucleic Acid

The procedure of Example 2 was repeated except for using firefly luciferase-specific siRNA (SEQ ID NOs: 3 (sense) and 4 (antisense); Elbashir, S. M., Nature (2001), 411: 494-498) instead of HBV-specific siRNA, to obtain the inventive composite containing firefly luciferase-specific siRNA, named DTC-Apo/siLuc.

EXAMPLE 4

Preparation of the Inventive Composite Containing Nucleic Acid

The procedure of Example 2 was repeated except for using 0.3 mg of a plasmid phRL-CMV encoding Renilla luciferase (Promega, WI) and 3 mg of DTC-Apo instead of 40 µg of HBV-specific siRNA and 400 µg of DTC-Apo, to obtain the inventive composite containing a plasmid phRL-CMV, named DTC-Apo/RLuc.

EXAMPLE 5

Preparation of the Inventive Composite Containing Nucleic Acid

The procedure of Example 2 was repeated except for using control double stranded RNA (SEQ ID NOs: 5 (sense) and 6 (antisense)) instead of HBV-specific siRNA, to obtain the inventive composite containing control double stranded RNA, named DTC-Apo/siCont.

COMPARATIVE EXAMPLES 1 to 4

Preparation of the Comparative Composite Containing Nucleic Acid

The procedures of Examples 2 to 5 were repeated except for using DTC instead of DTC-Apo, to obtain comparative composites named DTC/siHBV, DTC/siLuc, DTC/RLuc and DTC/siCont, respectively.

TEST EXAMPLE 2

Characterization of the Inventive and Comparative Composite

The inventive and comparative composites obtained in Examples 2 to 5 and Comparative Examples 1 to 4 were characterized by measuring their size and charge using a Zetasizer 3000 apparatus (Malvern Instruments, Malvern, Worcestershire, United Kingdom), respectively, to determine the average diameters and zeta potential values thereof. The results are shown in Table 1.

TABLE 1

| Formulation | Size (nm) | ζ pot (mV) |
|---|---|---|
| DTC | 176.5 ± 1.4 | 53.3 ± 4.0 |
| DTC with DNA | 205.5 ± 4.2 | 42.7 ± 1.8 |
| DTC with siRNA | 196.0 ± 1.8 | 44.6 ± 2.2 |
| DTC-Apo | 147.9 ± 2.8 | 49.5 ± 6.3 |
| DTC-Apo with DNA | 179.5 ± 3.4 | 38.6 ± 4.0 |
| DTC-Apo with siRNA | 177.1 ± 1.4 | 39.1 ± 2.8 |

As shown in Table 1, the inventive composite has an average particle size in the nanoscale range, suitable for systemic administration, and it is positive charged no matter whether it contained a nucleic acid or not, which showed that the inventive composite would not occur undesirable interaction with unknown serum components.

TEST EXAMPLE 3

Liver-Specific Gene Delivery In Vivo

In order to facilitate the systemic and sensitive detection of the in vivo migration route, Apo A-I of DTC-Apo/RLuc obtained in Example 4 was labeled with 0.6 mCi $^{131}$I (The Korea Atomic Energy Research Institute, Daejeon, South Korea) by the chloramines-T method (named DTC-Apo*/RLuc). 200 μCi of the purified DTC-Apo*/RLuc was intravenously injected into nude mice (Charles River Laboratories), and the radioactivity from the whole body of each mouse was monitored using a gamma-camera (Medical imaging Electronics, USA) at 40, 120 and 240 min postinjection, respectively. The results are shown in FIG. 2A.

Figure 2A:
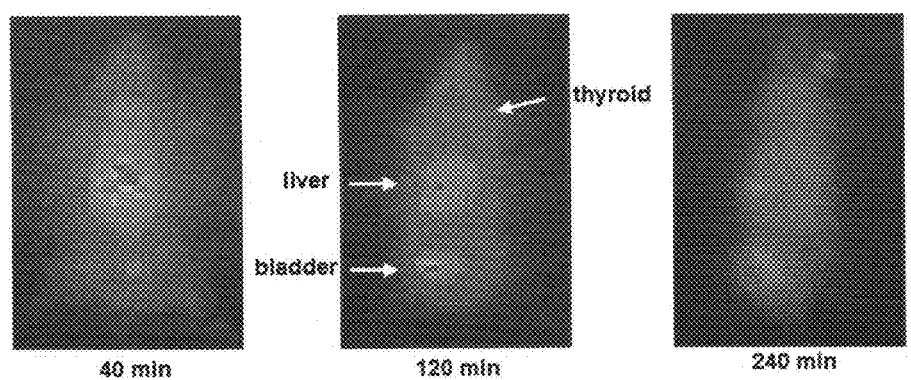
FIG. 2A: Whole body images for radioiodine signals captured using a gamma camera in a mouse intravenously injected with the inventive composite (DTC-Apo*/RLuc) which contains a Renilla luciferase expression plasmid, phRL-CMV and $^{131}$I label.

FIG. 2A clearly shows that the inventive composite is accumulated in the hepatic tissue at 40 min after administration.

Further, the cationic liposomes of the comparative and inventive composites, DTC/RLuc and DTC-Apo/RLuc obtained in Comparative Example 3 and Example 4, respectively, were labeled with a fluorescent dye, rhodamine using lissamine rhodamine B-diacyl phosphatidylethanolamine (Avanti Polar Lipids), to obtain labeled composities, DTC*/RLuc and DTC*-Apo/RLuc, respectively. The labeled composites were each injected into nude mice (Charles River Laboratories), and the whole body was monitored using IVIS 200 imaging system (Xenogen, USA) at 20, 60 and 100 min postinjection.

Figure 2B:
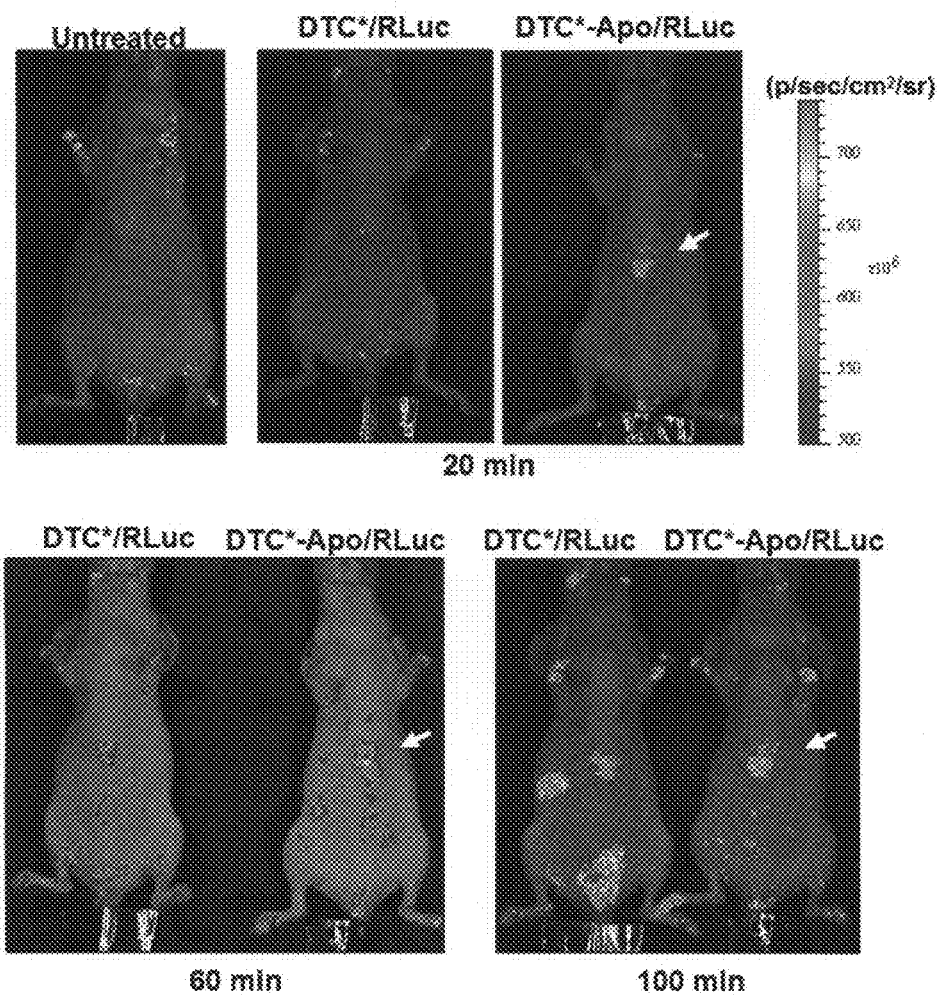
FIG. 2B: Whole body images captured several times after mice were intravenously injected with the inventive composite (DTC*-Apo/RLuc) and a comparative composite (DTC*/RLuc), which are labeled with rhodamine, respectively.

As shown in FIG. 2B, the accumulation level of the inventive composite is enhanced in the liver more prominently than that of the comparative composite. The fluorescent signal noise detected at the ends of the limb may be due to the overlapped emission wavelengths between rhodamine and red blood cells.

Further, in order to examine nucleic acid release by the inventive composite after systemic injection, mice (Charles River Laboratories) were intravenously treated with 200 μCi of the unlabeled DTC/RLuc or DTC-Apo/RLuc, or naked phRL-CMV or a 5% dextrose solution, as controls, and sacrificed the following day. Heart, lung, kidney and liver were each harvested from each mouse and homogenized. The bioluminescent intensity of each tissue homogenate was measured using a renilla luciferase assay system (Promega) to determine the luciferase expression level per total protein. The results are shown in FIG. 2C.

Figure 2C:
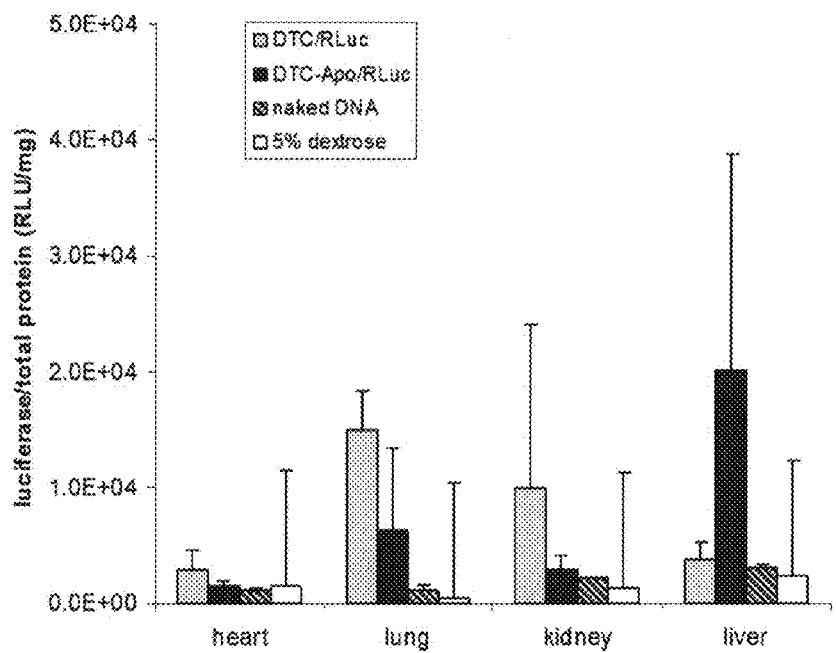
FIG. 2C: Luciferase levels measured in tissue homogenates from heart, lung, kidney and liver of mice (n=3) which were intravenously administered with a mock control (5% dextrose), naked DNA, or the inventive or a comparative composite containing a Renilla luciferase expression plasmid, phRL-CMV (DTC/RLuc or DTC-Apo/RLuc)

As shown in FIG. 2C, consistently with liver-specific accumulation of isotope or rhodamine-labeled DTC-Apo composites (FIGS. 2A and 2B), luminescence signals are particularly prominent in the liver of mice injected with DTC-Apo/RLuc in an amount ranging from 6,700 to 50,300 RLU/mg. In contrast, in mice treated with DTC/RLuc, luciferase signals were strong in the lung and kidney but only modest in the liver.

The results suggest that the inventive composite can liver-specifically deliver a therapeutic gene or drug to hepatic cells the therapeutic gene being expressed therein.

TEST EXAMPLE 4

Therapeutic Effect of the Inventive Composite with Nucleic Acid

To examine the therapeutic activity of the inventive composite, in vivo antiviral effect of DTC-Apo containing HBV-specific siRNA (DTC-Apo/siHBV) was examined using a mouse model for acute HBV infection as follows.

First, in order to establish an acute HBV-infected mouse model, HBV replication competent plasmid, pCpGHBV-MBRI, was created by excision of the viral genome from the mother clone pHBV-MBRI (Shin, D., et al., *Virus Res.* (2006), 119: 146-153) and religated into SpeI and XbaI digested pCpG-mcs (InvivoGen, USA), which is known to be not inducible nonspecific inflammatory responses in mammalian hosts. Then, 10 μg of pCpGHBV-MBRI was hydrodynamically injected into the tail veins of female C57BL/6 mice (Charles River Laboratories) of 8-9 weeks of age weighing approximately 20 g to induce the acute HBV infectious. After 8 hours, the HBV-infected model mice were intravenously administered with 2 mg/kg (i.e., 40 μg of nucleic acid per mouse) of DTC-Apo/siHBV, DTC-Apo/siCont, DTC/siHBV and DTC/siCont obtained in Examples 2 and 5, and Comparative Examples 1 and 4, respectively. 2 mg/kg of naked HBV-specific siRNA or 5% dextrose solution was also administrated to control mice groups. Serum samples were collected from each treated mouse on days 2, 4, 6 and 8 after injection, and the serum HBV surface antigen (HBsAg) level, one of the major viral structural proteins, was determined by ELISA (DiaSorin, USA) to monitor the viral protein level secreted into the blood. The results are shown in FIG. 3A.

Figure 3A:
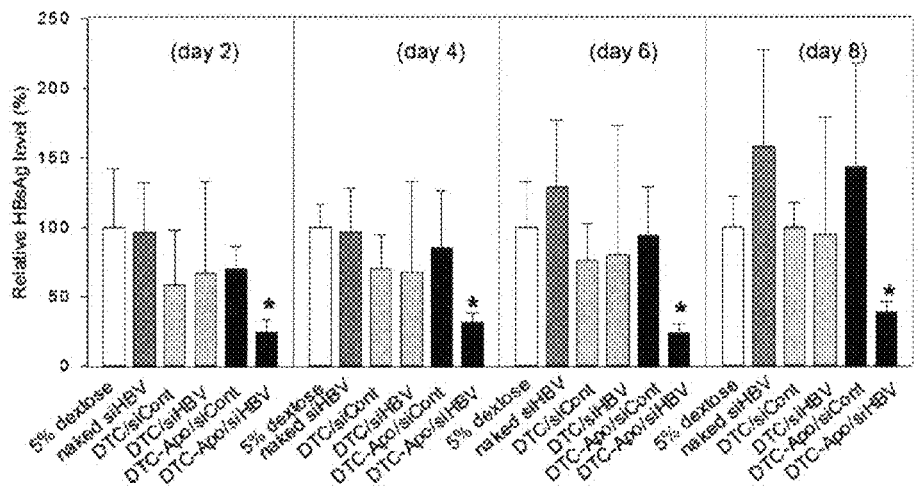
FIG. 3A: Relative levels of secreted HBsAg determined by ELISA in mice which were intravenously injected with a mock control (5% dextrose); naked siHBV; comparative composites containing HBV-specific siRNA (DTC/siHBV) and irrelevant control siRNA (DTC/siCont); and the inventive composites containing HBV-specific siRNA (DTC-Apo/si- HBV) and irrelevant control siRNA (DTC-Apo/siCont), respectively, at days 2, 4, 6 and 8 after the injection.

As shown in FIG. 3A, there is a significant reduction of serum HBsAg in mice administered with a single dose of DTC-Apo/siHBV particles, as shown by the average inhibitions degree of 65.1% (P=0.014), 63.4% (P=0.047), 74.9% (P=0.015) and 72.8% (P=0.034) on days 2, 4, 6 and 8 post-injection, respectively, relative to the matched DTC/siHBV or DTC-Apo/siCont treated mice.

Further, in order to examine the dose-dependent activity of DTC-Apo/siHBV, the mice with acute HBV replication were treated with 0.5, 1, or 2 mg/kg doses of DTC-Apo/siHBV, while 2 mg/kg of DTC-Apo/siCont or a 5% dextrose solution was also administrated to the model mice as control groups. The serum viral antigen levels in each mouse was monitored at day 4 post-injection. The results are shown in FIG. 3B.

Figure 3B:
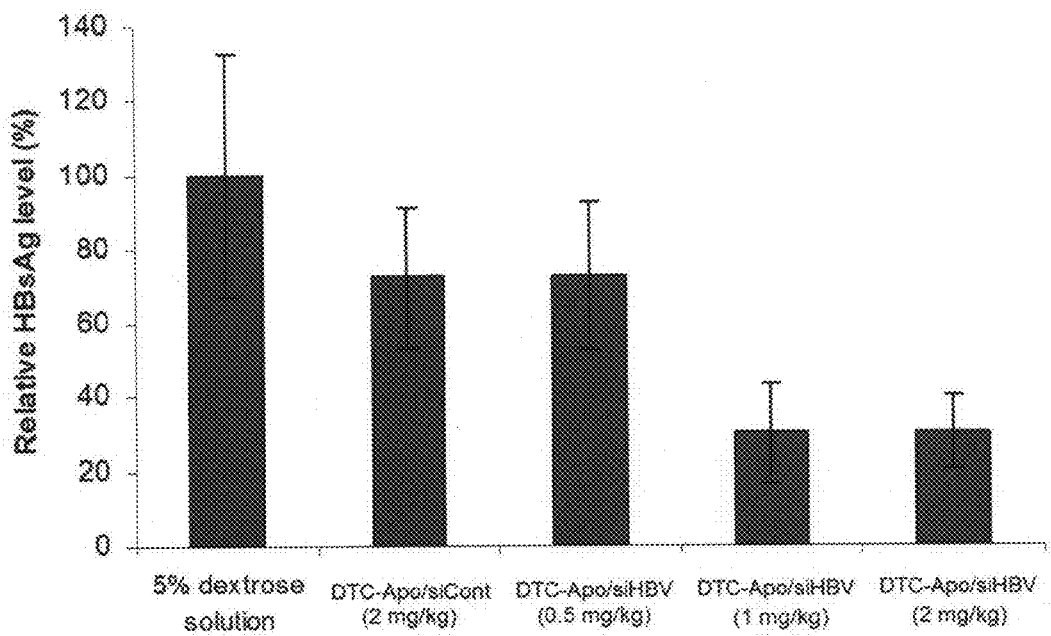
FIG. 3B: Serum HBsAg levels measured by ELISA in in vivo mouse models of HBV replication which were intravenously injected with the inventive composites containing HBV-specific siRNA (DTC-Apo/siHBV) and irrelevant control siRNA (DTC-Apo/siCont), respectively, at doses of 0.5, 1 or 2 mg/kg, at day 4 after the injection.

As shown in FIG. 3B, the treatment of the inventive composite containing HBV-specific siRNA reduces the viral antigen expression in mice with acute HBV replication in a does-dependent manner, unlike the control groups.

These in vivo data indicate that the inventive composite can promote the hepatic tissue-specific delivery of a therapeutic nucleic acid or drug and lead to potent therapeutic effects in vivo, only through a intravenous treatment of the inventive composite containing a therapeutic nucleic acid or drug.

TEST EXAMPLE 5

Therapeutic Effect of the Inventive Composite with Nucleic Acid

In order to confirm that the target-specific effect of the inventive composite comprising a therapeutic nucleic acid or drug occurs selectively and mainly in the hepatic tissue, 6-7-week-old female Balb/c mice (Charles River Laboratories) were hydrodynamically injected with 10 μg of pEGFPLuc plasmid (Clontech), which is known to express the firefly luciferase and also to facilitate in vivo image analysis, respectively.

After one day, DTC-Apo/siLuc or DTC-Apo/siCont obtained in Example 3 or 5, or a 5% dextrose solution control was injected at a dose of 1 mg/kg via the tail veins of the mice under ambient pressure, and the following day, the treated mice were anaesthetized with 2% isoflurane, and intraperitoneally injected with 200 μl of 15 mg/ml D-luciferin (Molecular Imaging Products Company, USA). Ten minutes later, photon signals from the whole body of each mouse was analyzed using an IVIS imaging system (Xenogen). The results are shown in FIGS. 4A and 4B.

Figure 4A:
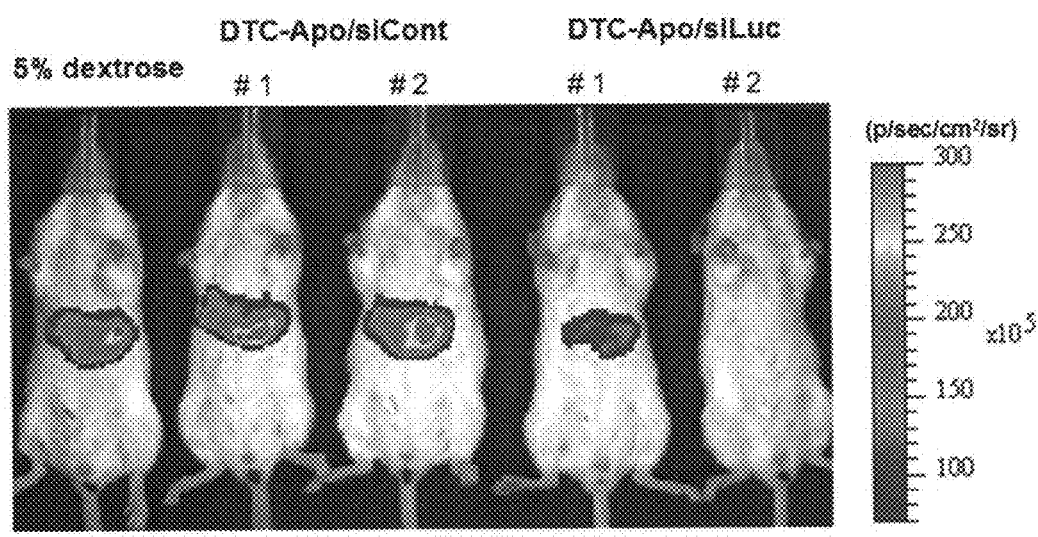
FIG. 4A: In vivo images of luciferase gene expression in mice which were administered with a luciferase expression plasmid, pEGFPLuc, and one day after administration, intravenously injected with the inventive composites containing luciferase-specific siRNA (DTC-Apo/siLuc) or irrelevant control siRNA (DTC-Apo/siCont), respectively.
Figure 4B:
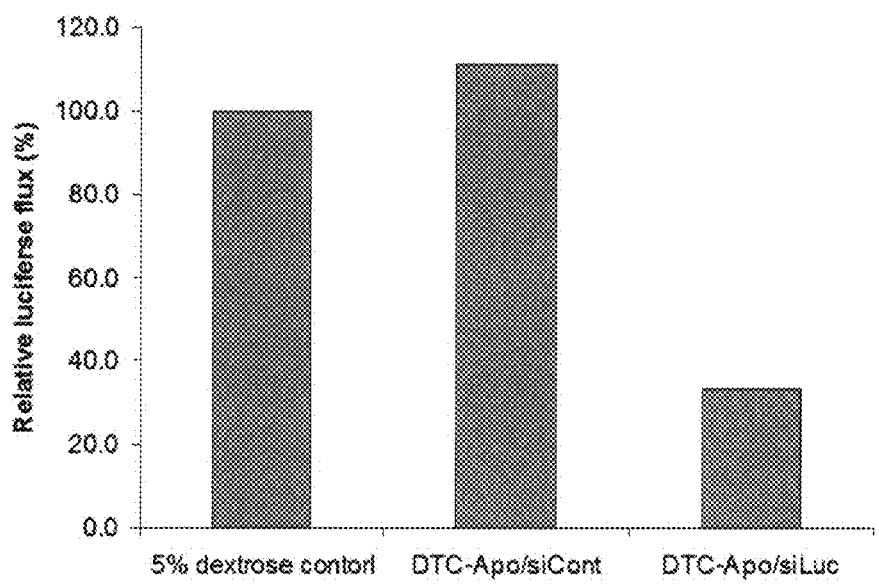
FIG. 4B: Relative luciferase expression levels measured by counting bioluminescent signals emitted from the liver of the mice shown in FIG. 4A.

As shown in FIGS. 4A and 4B, there is no signal change suggesting luciferase expression inhibition in mice injected with DTC-Apo/siCont, while a dramatic reduction in luciferase activity (about 70%) was observed for mice treated with DTC-Apo/siLuc as early as day 1 after treatment.

Taken together, these results show that the selective target of the inventive composite administered systemically is the liver and that the therapeutic nucleic acid or drug delivered by the inventive composite is specifically released into hepatic cells to manifest a potent therapeutic effect, without inducing any enzymatic abnormalities or pathological damage of the normal liver function.

While the embodiments of the subject invention have been described and illustrated, it is obvious that various changes and modifications can be made therein without departing from the spirit of the present invention which should be limited only by the scope of the appended claims.

What is claimed is:

1. A composition comprising:
   an isolated composite of an apolipoprotein A-1 and a liposome-forming material, said liposome-forming material being a mixture of 1,2-dioleoyl-3-trimethylammonium-propane and cholesterol, forming a liposome;
   a pharmaceutically acceptable carrier; and
   an isolated therapeutic agent which is targeted to be delivered to and released in the liver of a subject who is in need of receiving the therapeutic agent, encapsulated within the liposome.

2. The composition according to claim 1, wherein the therapeutic agent is a therapeutic nucleic acid.

3. The composition according to claim 2, wherein the therapeutic nucleic acid is an siRNA specific for HBV or HCV genome.

4. The composition according to claim 1, wherein the weight ratio of the apolipoprotein A-1 and the liposome-forming material is in the range of 1: 0.1 to 1: 1000.

5. The composition according to claim 1, wherein the therapeutic agent is an active polypeptide, an anticancer agent or an antivirus agent.

6. The composition according to claim 5, wherein the active polypeptide is selected from the group consisting of epidermal growth factor, erythropoietin, coagulation factors VIII, IX and VIIa, follicle stimulating hormone, granulocyte colony-stimulating factor, granulocyte-macrophage colony stimulating factor, insulin, insulin-like growth factor, interferon-α, -β and -γ, interleukin-1, -2, -11, -12 and -15, parathyroid hormone, platelet-derived growth factor, human growth hormone, tissue plasminogen activator, vascular endothelial growth factor, and a mixture thereof.

7. The composition according to claim 5, wherein the anticancer agent is selected from the group consisting of carboplatin, cisplatin, oxaliplatin, heptaplatin, etoposide, semustine, hydroxycarbamide, citarabine, fludarabine, doxorubicin, epirubicin, idarubicin, pirarubicin, fluorouracil, fluoxuridine, mitomycin, bleomycin, clofazimine, interferon, streptozocin, gemcitabine, enocitabine, capecitabine, ursodeoxycholic acid, sorafenib, tegafur, holmium, a holmium-chitosan complex, and a mixture thereof.

8. The composition according to claim 5, wherein the antivirus agent is selected from the group consisting of atazanavir, ribavirin, zanamivir, acyclovir, entecavir, didanosin, nevirapine, valaciclovir, nelfinavir, efavirenz, ganciclovir, lamivudine, famciclovir, stavudine, abacavir, indinavir, oseltamivir, inosiplex, adefovir, and a mixture thereof.

* * * * *

SEQUENCE LISTING

```
<160> NUMBER OF SEQ ID NOS: 6

<210> SEQ ID NO 1
<211> LENGTH: 19
<212> TYPE: RNA
<213> ORGANISM: Artificial Sequence
<220> FEATURE:
<223> OTHER INFORMATION: Synthetic construct (sense strand of siRNA
      specific for HBV)

<400> SEQUENCE: 1
gaggacucuu ggacucuca                                               19

<210> SEQ ID NO 2
<211> LENGTH: 19
<212> TYPE: RNA
<213> ORGANISM: Artificial Sequence
<220> FEATURE:
<223> OTHER INFORMATION: antisense strand of siRNA specific for HBV

<400> SEQUENCE: 2
ugagagucca agaguccuc                                               19

<210> SEQ ID NO 3
<211> LENGTH: 19
<212> TYPE: RNA
<213> ORGANISM: Artificial Sequence
<220> FEATURE:
<223> OTHER INFORMATION: Synthetic (sense strand of siRNA specific for
      luciferase)

<400> SEQUENCE: 3
cuuacgcuga guacuucga                                               19

<210> SEQ ID NO 4
<211> LENGTH: 19
<212> TYPE: RNA
<213> ORGANISM: Artificial Sequence
<220> FEATURE:
<223> OTHER INFORMATION: Synthetic (antisense strand of siRNA specific
      for luciferase)

<400> SEQUENCE: 4
ucgaaguacu cagcguaag                                               19

<210> SEQ ID NO 5
<211> LENGTH: 19
<212> TYPE: RNA
<213> ORGANISM: Artificial Sequence
<220> FEATURE:
<223> OTHER INFORMATION: Synthetic (Control siRNA)

<400> SEQUENCE: 5
gcaccuauaa caacgguag                                               19
```

```
<210> SEQ ID NO 6
<211> LENGTH: 19
<212> TYPE: RNA
<213> ORGANISM: Artificial Sequence
<220> FEATURE:
<223> OTHER INFORMATION: Synthetic (Control siRNA)

<400> SEQUENCE: 6
cuaccguugu uauaggugc                                                    19
```